United States Patent [19]

Leight

[11] Patent Number: 5,280,845
[45] Date of Patent: Jan. 25, 1994

[54] EARPLUG DISPENSER

[76] Inventor: Howard S. Leight, 1330 Colorado Ave., Santa Monica, Calif. 90404

[21] Appl. No.: 961,432

[22] Filed: Oct. 15, 1992

[51] Int. Cl.$^5$ .............................................. G07F 11/54
[52] U.S. Cl. .......................................... 221/2; 221/1; 221/22; 221/186; 221/197; 221/203; 221/258; 221/264; 221/265; 221/277; 221/281; 221/287
[58] Field of Search ...................... 221/1, 2, 13, 14, 22, 221/89, 90, 64, 65, 174, 186, 189, 196, 197, 200, 203, 258, 264, 265, 277, 281, 287; 141/1, 2, 18, 21, 98, 114, 363, 364

[56] References Cited

U.S. PATENT DOCUMENTS

| | | | |
|---|---|---|---|
| 408,466 | 8/1889 | Dreimiller et al. | 221/15 X |
| 953,471 | 12/1909 | Kuhn | 221/196 |
| 975,978 | 3/1910 | Moore | 221/196 |
| 1,929,788 | 10/1933 | Myers et al. | 221/264 |
| 2,550,884 | 4/1947 | Tandler | 221/258 X |
| 2,853,172 | 8/1954 | Angell | 221/5 X |
| 3,016,167 | 12/1958 | Richards | 221/235 |
| 3,101,872 | 8/1963 | Dickinson | 221/265 X |
| 3,410,451 | 11/1968 | Wilmer | 221/13 |
| 3,811,599 | 5/1974 | O'Connor | 221/265 |
| 3,894,657 | 7/1975 | Eckmayr | 221/265 |
| 4,109,825 | 8/1978 | Weitzman | 221/14 |
| 4,308,974 | 1/1982 | Jones | 221/196 |
| 4,428,502 | 1/1984 | Veltri | 221/196 X |
| 4,457,451 | 7/1984 | Ichikawa | 221/200 X |
| 4,555,624 | 11/1985 | Steffen | 221/2 X |
| 4,573,606 | 3/1986 | Lewis et al. | 221/2 |
| 5,143,252 | 9/1992 | Shi | 221/287 X |
| 5,176,290 | 1/1993 | Schwarzli | 221/200 X |

FOREIGN PATENT DOCUMENTS

3601232  7/1987  Fed. Rep. of Germany.

Primary Examiner—H. Grant Skaggs
Assistant Examiner—Dean A. Reichard
Attorney, Agent, or Firm—Arthur Freilich; Robert D. Hornbaker; Leon D. Rosen

[57] ABSTRACT

An apparatus is described which can receive a large number of earplugs from a box and dispense one or two of them at a time to a worker, which avoids touching of the earplugs by any other person. The apparatus includes a wheel (22, FIG. 1) which is rotatable on a frame (12) and which has holes (24) that are each capable of holding a single earplug (26). As the wheel turns, earplugs fall into the holes. As each hole moves to a dispense location (30), the earplug in the hole can fall out of the hole along a dispense passage (16). A barrier (42) lying above the wheel, prevents an earplug from falling into a hole that lies at the dispense location, and sweeps away any second earplug which lies partially within a hole approaching the dispense location. A large number of earplugs are contained in a box (80) which is installed in an open top (82) of the dispenser. With the box installed, a handle end (132) of a release device, is pulled, to peel a strip of tape of the release device away from adjacent edges of two bottom flaps of the box, to allow the flaps to pivot down under the weight of earplugs. In an electric motor-powered dispenser, a sensor device (218, FIG. 11) detects the drop of each earplug along the dispense passage (210), to stop energizing the motor that turns a dispense wheel (202) after two earplugs have been dispensed. Thus, even if some holes of the wheel do not receive an earplug, two earplugs will always be dispensed.

14 Claims, 5 Drawing Sheets

EARPLUG DISPENSER

BACKGROUND OF THE INVENTION

Large numbers of disposable earplugs are used in industrial plants, with each worker taking a pair of earplugs at a time. In some situations, a large box of earplugs is opened, and workers place their hands in the box to pick up a pair of earplugs. If a worker picks up more than two earplugs, he may simply throw the additional ones away. Furthermore, if a worker has dirty hands, he may leave dirt on other earplugs which other workers do not want to use. Another approach is to place each pair of earplugs in a separate plastic bag. The disposable earplugs may cost only several pennies apiece, so the need to place pairs of them in separate packages can add substantially to the cost of a box of several hundred earplugs. A dispenser which enabled "loose" earplugs to be used, with minimal wastage by workers taking more than two earplugs at a time and which avoided soiling of earplugs as a result of handling by workers, would be of considerable value.

SUMMARY OF THE INVENTION

In accordance with one embodiment of the present invention, an earplug dispensing apparatus is provided for facilitating the dispensing of earplugs while avoiding soiling or loss of earplugs prior to dispensing. The apparatus includes a wheel rotatable on a frame and having holes that each can hold a single earplug. As the wheel turns, earplugs drop from a bin or hopper into the wheel holes which carry them to a dispense location at which each earplug drops out of a hole. A barrier lies above an approach to the dispense location, to prevent an earplug from falling into the wheel hole thereat as well as to sweep away a second earplug that initially lies partially in the hole.

A large number of earplugs lying loosely in a box, can be loaded into the hopper without requiring contact with a worker's hands and without the likelihood of some earplugs dropping onto the floor. The closed box is pushed down into an open top of the frame, with a pair of flaps at the lower end of the box held together by a release device. The release device includes a strip of tape that adheres to adjacent outer ends of the bottom flaps. With the box fully installed, a person grasps an end of the release device, which projects from an opening in the frame, to peel away the strip of tape from the flap outer end. This allows the flaps to pivot down under the weight of earplugs, and allow the earplugs to fall down into the hopper.

In an automatic dispenser, an earplug holding station lies along the dispense passage to retain a pair of earplugs until a worker removes them from the holding station. An electric motor is coupled to the wheel to turn it. A sensor detects each earplug dropping along the dispense passage to the holding station. A control coupled to the sensor and motor, causes the motor to turn the wheel to repeatedly dispense earplugs, until the sensor senses that a predetermined number of earplugs, such as two, have dropped along the passage, and then stops the motor. When a worker removes the earplugs from the holding station, the control automatically energizes the motor again until two more earplugs have been dispensed and are waiting in the holding station.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
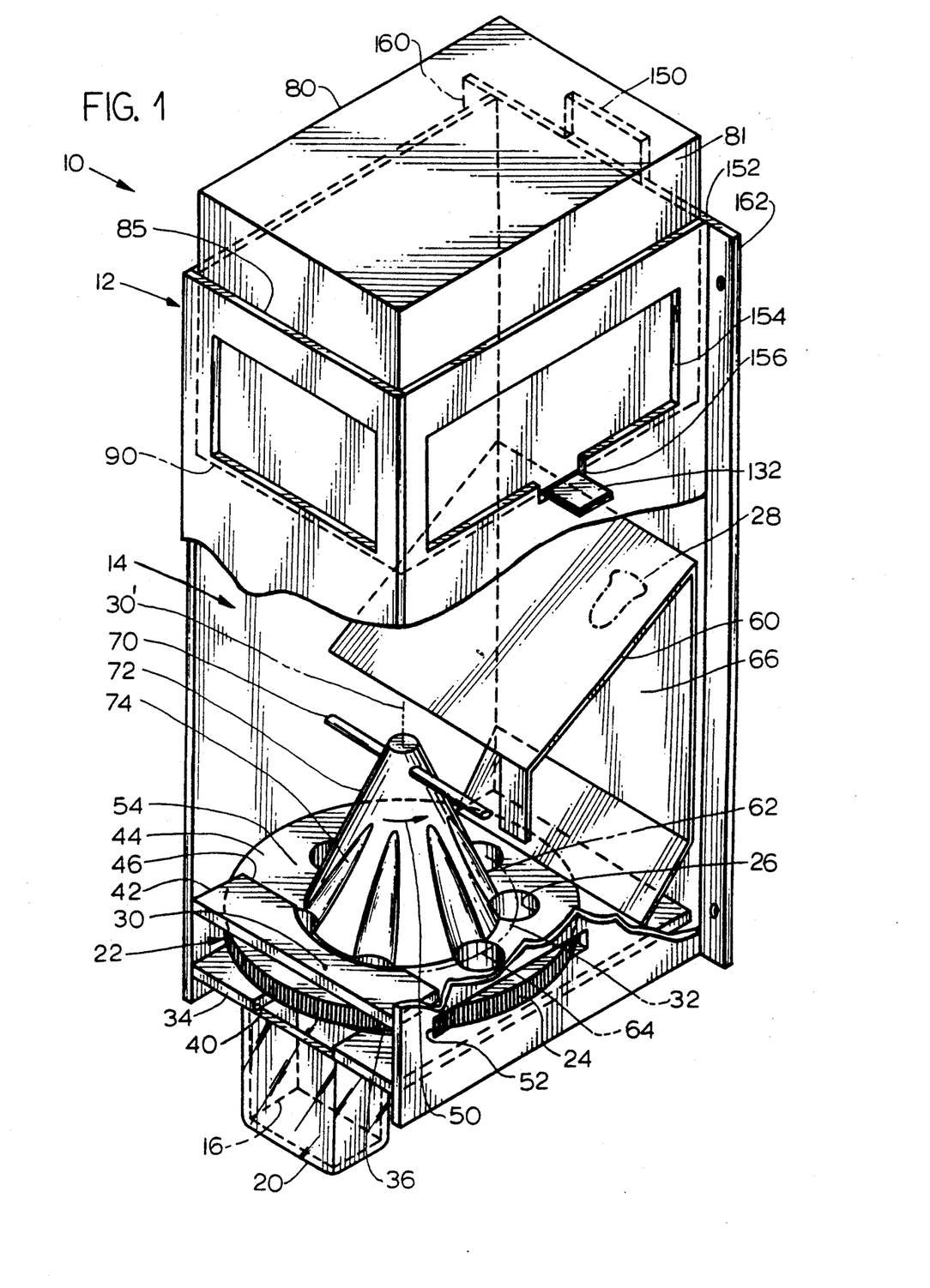
FIG. 1 is an isometric view of an earplug dispenser, with part of the frame broken away.
Figure 2:
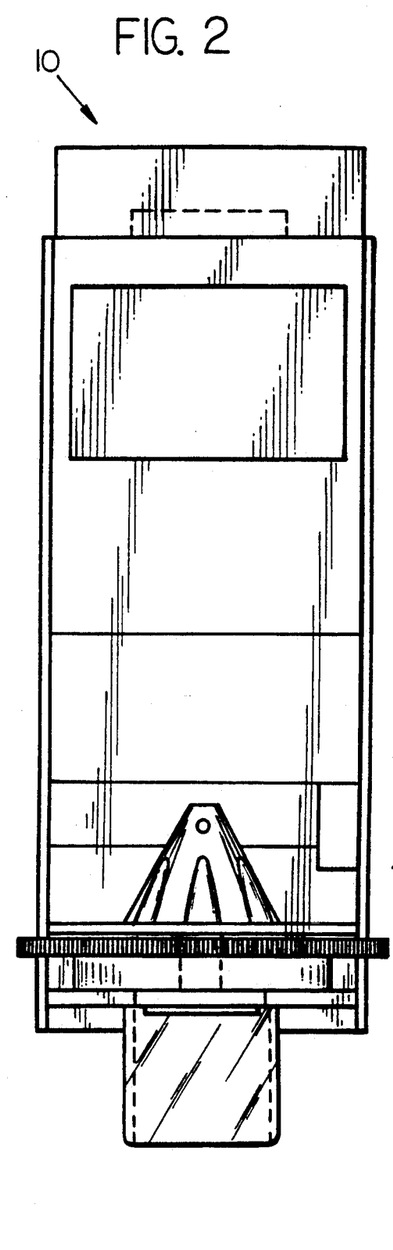
FIG. 2 is a front elevation view of the dispenser of FIG. 1.

FIG. 1 illustrates an earplug dispenser 10 which includes a frame 12 that forms a bin or hopper (which may or may not be tapered) 14. The hopper 14 holds a large number of earplugs such as several hundred of them when filled. The earplugs are dispensed one at a time through a dispense passage 16. A worker places one hand under the bottom 20 of the dispense passage, while turning a wheel 22 by pressing against a peripheral portion 24 of the wheel and moving it. The wheel has a plurality of holes 26 that are each large enough to hold a single one of the earplugs, with one earplug indicated at 28. The earplugs may be of the type described in U.S. Pat. No. 4,774,938. As the wheel turns, each hole 26, which generally has received a single earplug, passes to a dispense location 30 which lies over the dispense passage 16. The earplug in the hole drops out of the hole into the dispense passage, and into the waiting hand of the worker.

Disposable earplugs are used in large numbers in industry. At the beginning of the workday, and possibly after lunch and each work break, a worker may take another pair of earplugs which he will later throw away. Worker's hands often contain considerable dirt or grease, and if a worker dips his hand into a box of earplugs to pull out two, he may soil adjacent earplugs. There are disadvantages to packaging each pair of earplugs in a separate bag, in that the bag adds to the cost of the pair of earplugs, and may be annoying for the worker to open. The present dispenser allows each worker to obtain a pair of earplugs from a "loose" pile of them, while minimizing the possibility of a worker with dirty hands soiling other earplugs, and while avoiding wastage of earplugs that can occur when a worker picks up more than two earplugs and has to throw away the extra ones.

Figure 5:
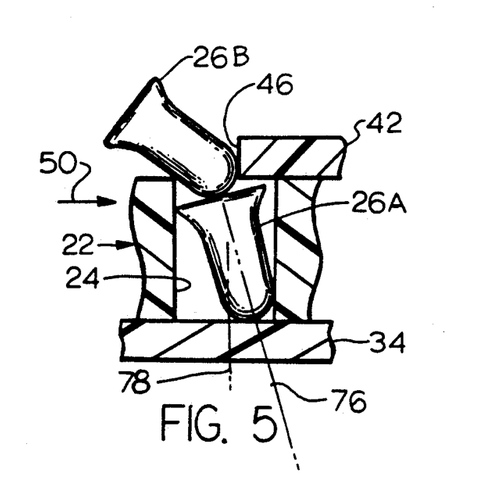
FIG. 5 is a sectional view of a portion of FIG. 1.

Referring again to FIG. 1, the wheel is rotatably mounted on the frame about an axis 30'. The wheel holes 26 are equally spaced from the axis of rotation, and move in a circular path 32 as the wheel turns. A retainer 34 is in the form of a plate, lies adjacent to the lower surface 36 of the wheel to prevent the earplugs from falling out of the wheel before they reach the dispense location. The retainer lies under the entire circular path of the holes, except for a cutout 40 where it forms part of the dispense passage 16. A barrier 42 lies immediately above the upwardly-facing top surface 44 of the wheel, to sweep away any second earplug that lies partially in one of the holes above a first earplug that lies fully in the hole. The barrier also blocks the space above the dispense passage 16, to prevent a second earplug from falling into one of the holes as an earplug falls out of the hole at the dispense location 30. Of course, the exact location where the earplug drops out of a hole varies slightly, depending on the direction of wheel rotation, etc. FIG. 5 shows how the leading edge 46 of the barrier 42 can sweep away a second earplug 28B which initially lies partially in a hole 26 above a first earplug 28A. It is assumed that the wheel 22 is moving in the direction of arrow 50.

Referring again to FIG. 1, it can be seen that the frame forms wheel-receiving openings 52 in three of its sides, through which a peripheral portion 24 of the wheel extends. The peripheral portion of the wheel is preferably roughened, as with knurling or the like, to facilitate turning, although it extends in substantially a circle. Although the peripheral portion of the wheel may be soiled, seals can be used within the frame to prevent such soiling from reaching the earplugs.

Figure 3:
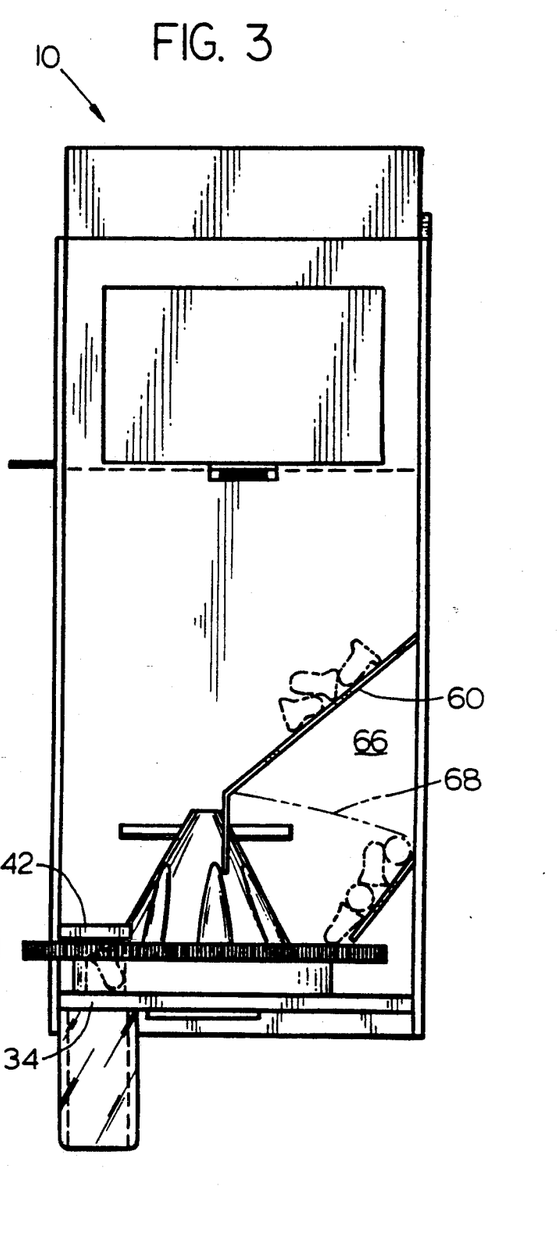
FIG. 3 is a side view of the dispenser of FIG. 1.
Figure 4:
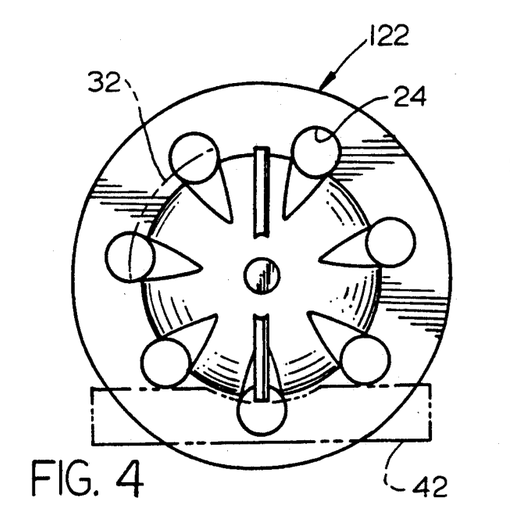
FIG. 4 is a plan view of the wheel of the dispenser of FIG. 1.

The frame preferably includes an inclined wall 60 lying above a first portion 62 of the circular path 32 of the wheel holes, but not above a second portion 64. If the hopper 14 is nearly completely filled with earplugs, the weight of the earplugs can tend to "jam" the earplugs together. Such "jamming" can prevent earplugs from falling into the wheel holes. The inclined wall 60 provides a jam-protected region 66 lying under the inclined wall, where earplugs are largely protected from jamming by the weight of a large number of earplugs above them. The earplugs stack up only to a height indicated at 68 in FIG. 3 to leave the jam-protected region 66. The wheel includes stir arms 70 that pass into and out of the jam-protected region 66 and a region 71 above the second portion of the path 64, to move the earplugs and avoid jamming.

The wheel 22 includes an upward projection 72 lying radially within the path of the wheel holes. The projection forms a plurality of inclined guideways 74 that are each positioned to guide an earplug in downwardly inclined motion into a corresponding one of the wheel holes 26. This aids in filling each hole with an earplug, by helping to align the earplug so the axis 76 (FIG. 5) of the earplug tends to align with the vertical axis 78 of the hole.

Whenever the supply of earplugs in the hopper 14 (FIG. 1) runs low, a new batch of earplugs is installed by dumping earplugs held in a box 80 into the frame 12. If the box were opened and tipped to pour the earplugs in a stream into the open top 85 of the frame, then several earplugs would be likely to miss the frame and fall on the floor, where they would be soiled and have to be picked up. Applicant facilitates the transfer of earplugs from the box 80 to the frame hopper 14, by constructing the frame top 85 so it can receive the box 80, and by constructing the box so it can be opened after full installation in the frame.

Figures 6, 8:
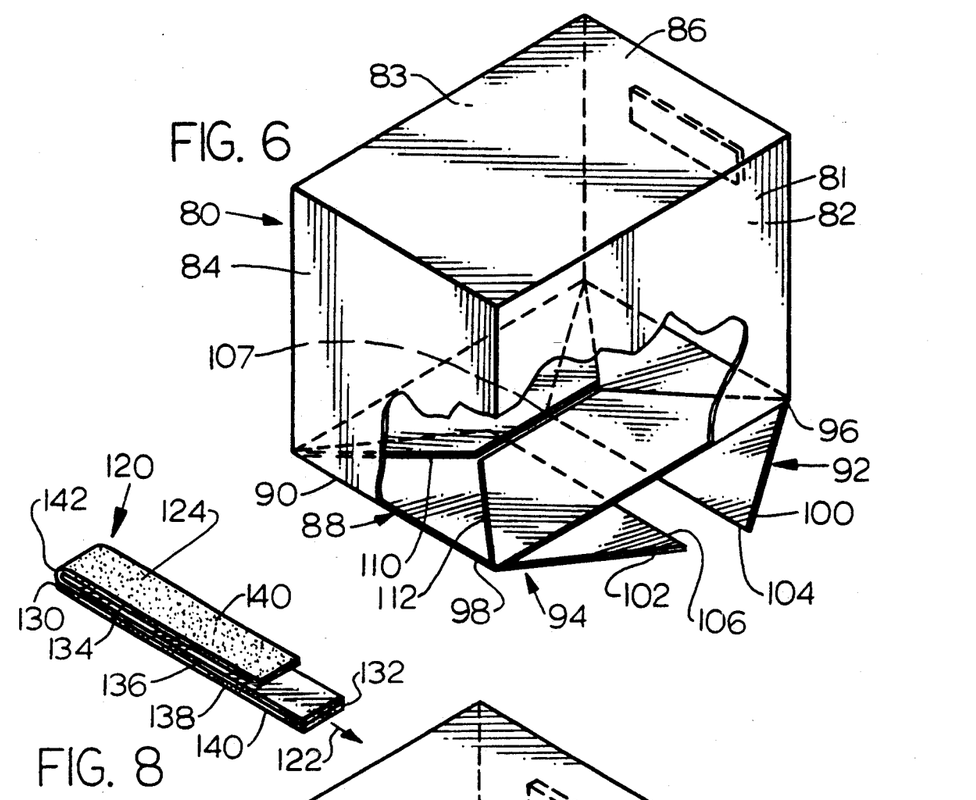
FIG. 6 is an isometric view of the earplug-holding box of FIG. 1, with a portion of the box side walls broken away, and with the release device fully removed and the box partially open.
FIG. 8 is an isometric view of the release device of the box of FIG. 7.

As shown in FIG. 6, the box 80 is of largely conventional construction, with four side walls 81-84, a top wall 86, and a bottom wall 88 at the lower end or bottom 90 of the box. The bottom wall includes a pair of flaps 92, 94 having inner flap edges 96, 98 pivotally mounted on the lower end of a corresponding side wall 82, 84. Each flap has an outer flap end 100, 102 that forms an outer edge 104, 106. The outer flap end 100 or edge 104, has first and second flap corners 107, 108 (which may be sharp or rounded).

Figure 7:
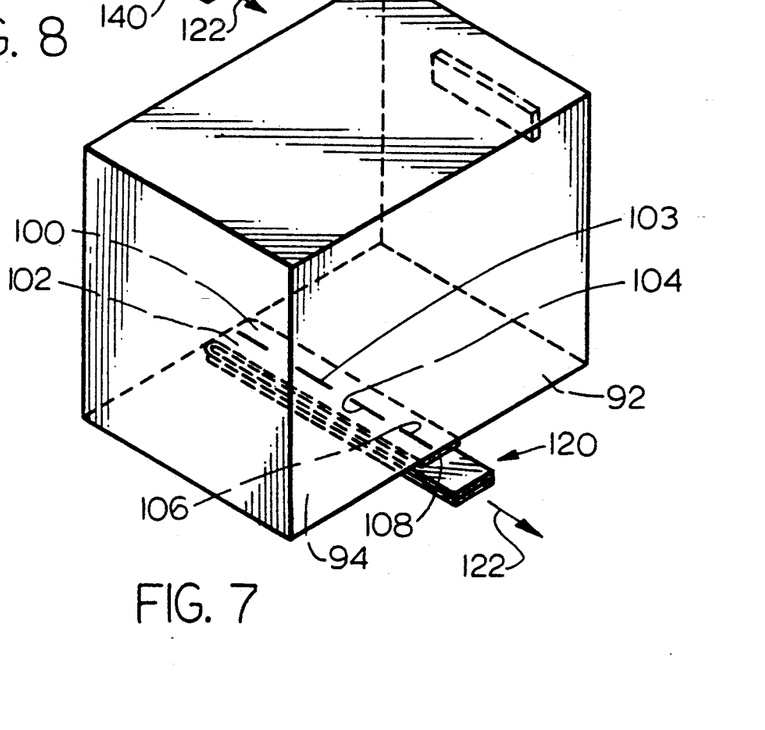
FIG. 7 is an isometric view of the box of FIG. 6, with the box fully closed and with the release device in place.

Each flap 92, 94 can be pivoted from a closed position shown in FIG. 7, to a partially opened position shown in FIG. 6, and to a fully opened position wherein the flaps 92, 94 both extend primarily vertically to allow earplugs in the box to fall out. It is noted that the box bottom wall 88 also includes a pair of upper leafs 110, 112 which have adjacent edges that are unjoined. It is possible to use the box without the leafs, although they help to prevent unintended opening of the box. When the outer ends 100, 102 of the flaps are not joined to each other or to the side walls, they and the leafs will pivot downwardly (their outer edges move down) to allow the earplugs to drop out.

Initially, the box is in the configuration shown in FIG. 7, wherein the flaps 92, 94 are kept closed by a release device 120 which holds the flap outer ends 100, 102 to each other in a joint 103. The release device can be pulled in a primarily horizontal direction 122 that is parallel to the lengths of the outer edges 104, 106 of the flaps to release the flap outer ends from each other so they and the leafs can pivot down and the earplugs can drop out.

As shown in FIG. 8, the release device 120 includes a flexible retain part or strip 124, which extends primarily parallel to the flap outer ends and edges and which joins them, the release strip extending between the first and second corners 106, 107 of each flap outer end. The handle has one end 130 that attaches to the end of the retainer strip lying at the first flap corner 106, and has an opposite projecting handle end 132 projecting beyond the opposite second flap corner 107. When the projecting handle end 132 is pulled in the release direction 122, the retainer strip 124 is progressively peeled off of the flaps to release their outer ends from each other and allow the flaps to pivot down.

Applicant can economically construct the release device of a strip of tape having first and second end portion 134, 136. The tape has an adhesive first face 140 which adheres the tape first end portion 134 to the flap outer ends. The adhesive face of the second, end portion 136 adheres the tape to a handle strip 141 which covers the adhesive face and strengthens the tape against tearing. The handle 138, comprising the tape second end portion 136 and the handle strip 141 can be stiff, since it does not have to bend in use (except that in the frame of FIG. 1, the projecting handle end 32 must bend during installation of the box. The retainer strip 124 is formed with a 180° fold at 142 which separates its first and second end portions. It is often desirable to lightly adhere the handle 138 to the second face of the tape first end portion 134, to keep the handle neatly held against the bottom of the box.

As shown in FIG. 1, the box 80 is installed in the top 85 of the frame, with the box in its fully closed position. The box moves down until a stop 150 on the box abuts a shoulder 152 on the frame. The stop can be anywhere along the side of the box (e.g. at the bottom), and the frame shoulder can lie at the top of the frame or below the top. As the box moves down into the frame, the projecting handle end 132 initially folds against the box side wall 81, and then flaps away from it into an opening 154 of the frame. The opening has a portion 156 designed specifically to receive the handle end 132 of the release device, with the lower end 90 of the box preferably lying substantially at the bottom of the frame opening portion 156. With the box thus installed, a person grasps the handle end 132 of the release device and pulls it, to open the bottom of the box and release the earplugs to fall into the bin or hopper 14.

It may be noted that, while applicant prefers to use two flaps at the bottom wall of the box, with their outer ends joined by a peelable strip, other variations are possible. Instead of using a tape which can be peeled off, it is possible to use a thin flexible wire which is progressively peeled off to progressively cut through a tape or the like as a handle end is pulled. Instead of using two lower flaps, it is possible to use a single flap which extends across substantially the entire bottom of the box, so the outer end of such flap lies adjacent to a vertical side wall of the box. In such a case, the outer end of the flap would be joined to an adjacent side wall of the box.

Applicant has constructed other boxes and release mechanisms. In one, the bottom wall of the box is formed of readily cut material such as a plastic sheet, and the upper part of the frame includes three blades that extend slightly inward of three sides of the box. In that case, when the box is laid in the frame and pushed down with force, the blades cut three sides of the box lower end, to leave a plastic flap with only one side joined to one side of the box, with the flap immediately falling down to empty the earplugs. Although such device was effective, it had the disadvantage of requiring cutting blades which might injure a worker.

The particular earplug dispenser 10 shown in FIG. 1, has a pair of flanges 160, 162 to enable the frame to be mounted on a wall. The relative simplicity of the dispenser enables it to be constructed at moderate cost and operate reliably.

Figure 9:
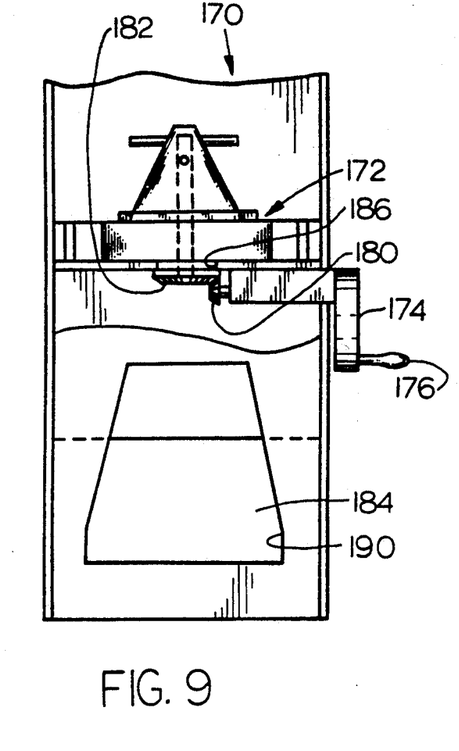
FIG. 9 is a partial sectional front view of an earplug dispenser constructed in accordance with another embodiment of the invention, wherein the wheel is turned by a gear-connected crank.
Figure 10:
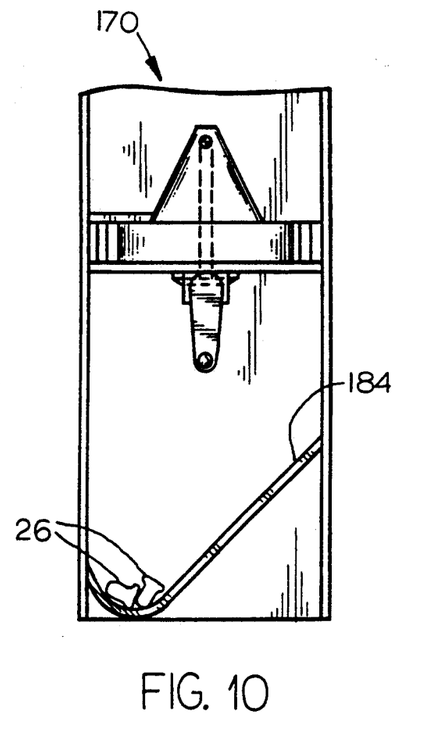
FIG. 10 is a sectional side elevation view of the dispenser of FIG. 9.
Figures 11, 12:
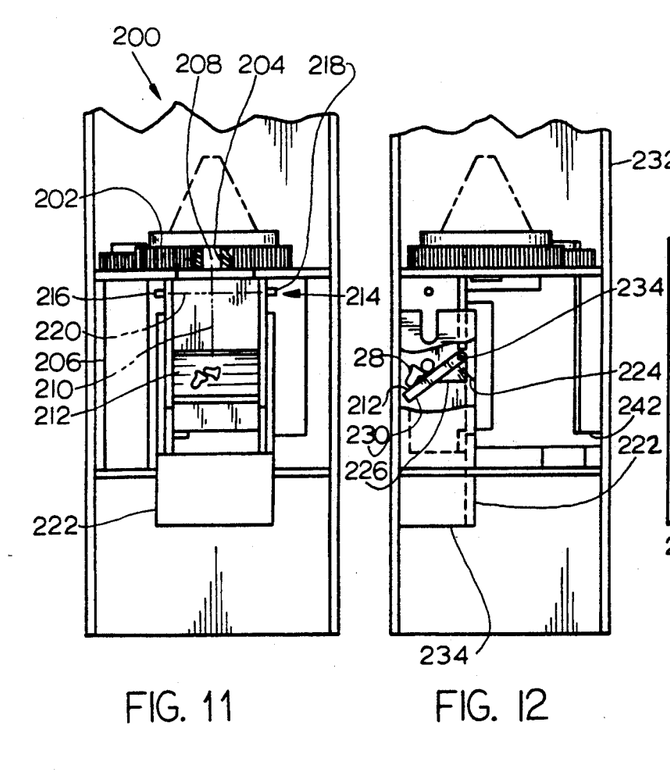
FIG. 11 is a partial front elevation view of an earplug dispenser constructed in accordance with another embodiment of the invention, wherein the wheel is turned by an electric motor and holds a pair of earplugs for rapid removal by a workman.
FIG. 12 is a side view of the dispenser of FIG. 11.

FIGS. 9-10 illustrate another earplug dispenser 170 which is of similar construction, but wherein the wheel 172 which has holes for receiving earplugs, is turned by a crank 174. A worker holds a handle 176 on the crank, to turn a shaft on which a bevel gear 180 is mounted. The gear 180 turns another gear 182 fixed to the wheel 172. As the wheel 172 turns, earplugs are dispensed in the same manner as for the dispenser of FIG. 1. However, the frame has a catcher 184 which catches earplugs falling along a dispense passage 186. An opening 190 in the frame allows a worker to extend his hand through the opening to pick up the earplugs 28 lying in the catcher.

FIGS. 11-14 illustrate another earplug dispenser 200 wherein the wheel 202 which has holes 204 for holding earplugs, is driven by an electric motor 206. As the wheel turns, earplugs in a hole such as 204, come to a dispense location 208 where the earplugs drop along a predetermined path 210 to an earplug holding station 212. A sensor device 214 which comprises a light beam source 216 and a light beam detector 218 lie on opposite sides of the dispense path. When an earplug falls along the dispense path 210, the earplug interrupts a light beam 220, which is detected by the photodetector 218. After the light beam 220 has been interrupted two times, to indicate that two earplugs have been dispensed, the motor 206 is no longer energized. However, when a person removes the earplugs from the holding station 212, a control senses this and reenergizes the motor to again dispense two earplugs.

Figure 13:
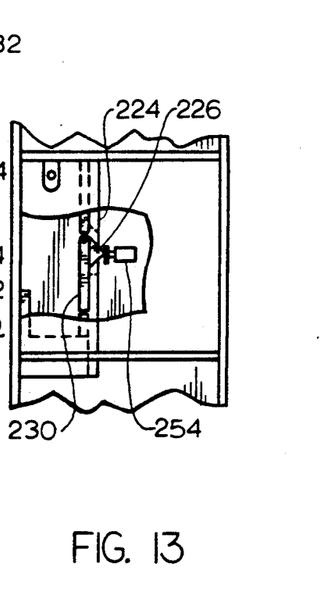
FIG. 13 is a partial side view of a portion of the dispenser of FIG. 12, with the holding station opened.

The particular mechanism for removing the earplugs includes a sleeve 222 (FIG. 12) which has a cam 224 that abuts a cam follower 226 on a retainer arm 230. The retainer arm is pivotally mounted on the frame 232, at a pivot location 234. When the sleeve 222 is lifted, it no longer prevents movement of the cam follower, and the retainer arm 230 moves down and allows the earplugs 26 at the holding station 212 to fall down through the sleeve and be caught in the hand of the person who is pushing upwardly on the bottom 234 of the sleeve. FIG. 13 shows the retainer arm 230 in the down position.

Figure 14:
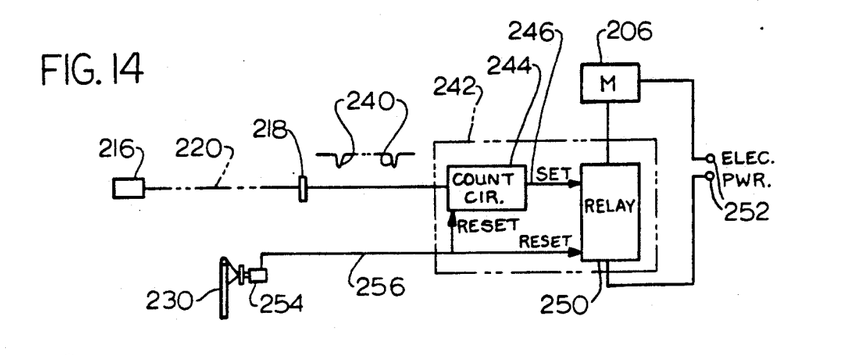
FIG. 14 is a block diagram of a circuit of the dispenser of FIG. 10.

As shown in FIG. 14, everytime an earplug interrupts the light beam 220, the photodetector generates a pulse 240. A control 242 includes a count circuit 244 which delivers a signal over line 246 after two pulses are received from the photodetector 218. The signal on line 246 sets a relay 250, to open the relay contacts. This prevents electricity from terminals 252 connected to an electrical power source, from energizing the motor. A holder detector 54, such as a switch, detects lowering of the retainer arm 230, and upon detecting such lowering delivers a signal over line 256 to the counting circuit 244 to reset it, and to the relay 250 to reset the relay. The reset relay is closed, and allows power to flow to the motor 206 to energize it. The motor turns the wheel until two more earplugs have been dispensed.

Thus, the invention provides an earplug dispenser and a box for refilling the dispenser, as well as methods for operating them, which facilitates the dispensing of earplugs while avoiding soiling of the earplugs and loss of earplugs while refilling the dispenser. The dispenser includes a rotatable wheel having a plurality of holes that are each capable of holding a single earplug. The frame of the dispenser includes a dispense passage lying below a location along the circular path of the holes, to enable an earplug to drop out of a hole. A retainer lies immediately below the wheel, but not at the dispense passage, and can form part of the dispense passage, to prevent earplugs from prematurely falling out of the holes. The frame also forms a barrier lying above the wheel at the dispense location, to prevent additional earplugs from falling into a wheel hole lying at the dispense location. The frame has a box-receiving top above a bin or hopper of the frame, for receiving a box that holds a multiplicity of earplugs. The box has a lower end that includes at least one flap with a free outer end that is prevented from moving down by a release device. The release device includes a flexible retain part which extends parallel to the outer end of the flap and which can be removed by pulling a handle on the release device, in a direction parallel to the outer edge of the flap. The box preferably includes two flaps with outer ends joined by the release device. When the box is installed, a handle end projects through an opening in the dispenser frame, to facilitate pulling of it. A motor-powered dispenser can be used, which includes a sensor device that detects the dispensing of an earplug, and a control coupled to the sensor device which energizes the motor to continue dispensing one earplug at a time until the sensor device detects the dispensing of two earplugs to a holding station. Another sensor detects when the pair of earplugs at the holding station is removed, to allow the motor to again cause dispensing of a pair of earplugs to the holding station.

Although particular embodiments of the invention have been described and illustrated herein, it is recognized that modifications and variations may readily occur to those skilled in the art, and consequently, it is intended that the claims be interpreted to cover such modifications and equivalents.

I claim:

1. An earplug container which is designed to be inserted into an open top of an earplug dispenser and then opened, to fill the dispenser without spilling earplugs on the floor, comprising:

a box having side, top, and bottom walls, said bottom wall closing a bottom of said box and said bottom wall including at least one flap having an inner flap edge pivotally mounted on the lower end of one of said side walls, said flap having an outer flap end with first and second opposite corners and forming an outer edge extending between said corners;

said flap being pivotable from a closed position wherein it closes at least part of said bottom of said box, downwardly to an open position wherein said flap outer end moves down to open said at least part of said bottom of said box and allow said earplugs to drop out;

a release device which holds said flap outer end to another portion of said box, and which can be pulled in a primarily horizontal direction to release said flap outer end so said earplugs can drop out, said release device including a flexible elongated retain part which extends primarily parallel to said flap outer end along most of the distance between said first and second opposite corners of said flap outer end and which can be removed to detach said flap outer end from said another portion of said box;

said release device includes a handle which is attached to said retain part and which extends across said box from substantially said first corner substantially to and beyond said second corner to leave a projecting handle end which can be grasped even when the entire bottom of said box is hidden, so said projecting handle end can be pulled to progressively peel away said retain part and release said flap to pivot down and allow said earplugs to drop out.

2. The container described in claim 1 wherein:
said retain part comprises a strip of tape which is peeled off said flap outer end as said handle is pulled.

3. The container described in claim 1 wherein:
said release device comprises a strip of tape, said strip of tape having first and second faces with adhesive on said first face;
said strip of tape having first and second end portions with a substantially 180° fold between them and with said adhesive first face lying on the outside of said fold, and said first end portion of said strip of tape forms said retain part and is adhesively joined to said flap outer end and to said another box portion;

a handle strip of flexible material which is adhesively joined to said first face of said second end portion of said strip of tape, with said handle strip and said second end portion of said strip of tape joined thereto, forming said handle of said release device.

4. The container described in claim 3 wherein:
said at least one flap includes a pair of bottom flaps each extending about halfway across said bottom of said box, with said bottom flaps having adjacent outer ends and having spaced inner edges that are each pivotally mounted on an opposite one of said side walls;
said first end portion of said strip of tape joins said adjacent outer ends of said bottom flaps, so when said handle is pulled said strip of tape is peeled away from said adjacent ends to allow both of them to pivot down.

5. The container described in claim 1 including
an earplug dispenser which includes a frame having an open top which closely receives a lower portion of said box, including said bottom walls and at least part of said side walls, said frame and box having shoulders that abut when said box is fully received in said frame, said frame having a side which lies adjacent to one of said box side walls of a box received in said open top, said frame side having an opening through which projects said projecting handle end of said release device handle of a fully received box.

6. An earplug dispenser comprising:
a holding station for receiving earplugs, said holding station being accessible by persons' hands to enable persons to remote the earplugs;
a mechanism which can be driven to normally dispense one earplug at a time along a predetermined path to said holding station;
a motor connected to said mechanism to drive it;
a sensor device which detects the dispensing of an earplug along said path;
a control coupled to said sensor device and said motor, said control constructed to energize said motor until said sensor device senses the dispensing of a predetermined number of earplugs, and to then stop energizing said motor, whereby to reliably dispense a predetermined number of earplugs.

7. The dispenser described in claim 6 wherein:
said sensor device includes a light beam detector and a source that directs a light beam at said detector, said detector detecting the interruption of said beam;
said mechanism is positioned so each dispensed earplug drops along said path onto said dispensing station;
said source is positioned to direct said beam at a location far enough above said holding station that it detects an earplug dropping along said path but not any of said predetermined number of earplugs resting at said holding station.

8. The dispenser described in claim 6 wherein:
said predetermined number is two, and said holding station is manually operable to release said pair of earplugs, to enable a user to take a pair of earplugs for his use; and including
a holder detector which generates a signal whenever said holding station is operated; and wherein
said control is coupled to said holder detector and is constructed to energize said motor until said sensor device detects the dispensing of another pair of earplugs, every time said holder detector generates a signal indicating operation of said holding station.

9. A method for filling an earplug dispenser that has an open top and a hopper thereunder, with earplugs initially held in a box having top, side, and bottom walls, where said bottom wall includes at least one flap with an inner end pivotally mounted on one of said side walls and an opposite outer end having an elongated outer edge, comprising:

installing said box in said top opening of said dispenser, with said box bottom wall lowermost but with said flap outer end joined to an adjacent box portion at a joint to keep said bottom wall closed;

with said box installed, separating said flap outer end from said adjacent box portion while leaving said flap inner end pivotally joined to said box side walls, and pivoting said flap downwardly about said inner end by the weight of said earplugs, to drop said earplugs into said dispenser hopper;

said step of separating including pulling an elongated flexible member extending along said joint where flap outer end is joined to said adjacent box portion, substantially in a direction parallel to said flap outer edge, to progressively remove said flexible member from said joint.

10. The method described in claim 9 including:

installing a strip that has first and second end portions and that forms said elongated flexible member, so said first end portion extends against and along said outer end of said flap and against an adjacent portion of said box and adheres to both said outer end and said adjacent portion to keep said flap closed, including bending said strip to form a 180° bend between said first and second end portions and extending said second end portion under and along said first end portion and beyond said first end portion;

said dispenser has a dispenser wall with an opening lying at about the height of said bottom wall of said installed box, and said step of installing includes projecting an end part of said strip second portion through said opening in said dispenser wall, and said step of pulling includes pulling on said end part to peel said first end portion of said strip from said flap outer end and said adjacent box portion after said box has been installed.

11. A method for dispensing pairs of earplugs at a time from a bin that holds a multiplicity of earplugs, comprising:

beginning to energize a motor driven mechanism that can, in the ideal situation, drop one earplug at a time from said bin along a dispense path into a holding station at predetermined intervals, but wherein said mechanism is unreliable in that it sometimes does not drop an earplug at each interval;

detecting each earplug falling along said dispense path;

ceasing to energize said motor after two earplugs are detected falling along said path;

detecting the removal of a pair of earplugs from said holding station;

again beginning to energize said mechanism upon said detection of removal.

12. Apparatus for dispensing earplugs comprising:
a frame;
a rotatable wheel rotatably mounted on said frame, said wheel having a plurality of holes that are each capable of holding a single one of said earplugs, said holes moving in a circular path as said wheel rotates;

said frame being constructed to hold earplugs that can drop into said wheel holes, and said frame having a box-receiving top and an opening with a portion lying below said top:

said frame forming a dispense passage lying below a dispense location along the path of said wheel holes as said wheel rotates, to enable an earplug lying in a hole that has moved to said dispense location to drop out of said hole, and said frame forming a retainer below part of said wheel but not at said dispense passage, to prevent earplugs from falling out of said holes before said holes reach said dispense location;

a barrier lying substantially above said wheel hole path at said dispense location, to prevent an earplug from falling into a wheel hole lying at said dispense location;

an earplug box for holding a multiplicity of earplugs, said box having a plurality of side walls, and said box having a lower end which can fit into said box-receiving top with said box lower end lowermost to install said box in said frame, said box lower end including at least one flap having an inner edge pivotally mounted on one of said side walls and having an opposite outer portion;

said flap being pivotable from a closed position wherein it closes said box lower end, to an open position wherein said outer portion moves down to open said box lower end and allow earplugs in said box to fall into said frame;

said box includes a release device which holds said flap outer portion to another portion of said box to prevent pivoting of said flap but with said release device capable of being pulled to remove it to stop holding said flap outer portion to said another portion, said release device having a handle with an end which projects out of said frame opening when said box is installed in said frame, to enable a person to grasp and pull said handle end to remove said release device and allow said flap to pivot to said open position so said earplugs can fall into said hopper.

13. Apparatus for dispensing earplugs comprising:
a frame;
a rotatable wheel rotatably mounted on said frame, said wheel having a plurality of holes that are each capable of holding a single one of said earplugs, said holes moving in a circular path as said wheel rotates;

said frame forming a hopper for holding earplugs that can drop into said wheel holes;

said frame forming a dispense passage lying below a dispense location along the path of said wheel holes as said wheel rotates, to enable an earplug lying in a hole that has moved to said dispense location to drop out of said hole, and said frame forming a retainer below part of said wheel but not at said dispense passage, to prevent earplugs from falling out of said holes before said holes reach said dispense location;

a barrier lying substantially above said wheel hole path at said dispense location, to prevent an earplug from falling into a wheel hole lying at said dispense location;

said hopper has an inclined wall lying above a first portion of said path but not above a second portion of said path, to leave a jam-protected region below said inclined wall which avoids the jamming together of earplugs above said path;

said wheel has a stir arm that projects into a region above said path but below at least part of said inclined wall, to move earplugs from a region above said second path portion into said jam-protected region to avoid jamming of earplugs lying above said second portion of said path.

14. Apparatus for dispensing earplugs comprising:

a frame;

a rotatable wheel rotatably mounted on said frame, said wheel having a plurality of holes that are each capable of holding a single one of said earplugs, said holes moving in a circular path as said wheel rotates;

said frame being constructed to hold earplugs that can drop into said wheel holes;

said frame forming a dispense passage lying below a dispense location along the path of said wheel holes as said wheel rotates, to enable an earplug lying in a hole that has moved to said dispense location to drop out of said hole, and said frame forming a retainer below part of said wheel but not at said dispense passage, to prevent earplugs from falling out of said holes before said holes reach said dispense location;

a barrier lying substantially above said wheel hole path at said dispense location, to prevent an earplug from falling into a wheel hole lying at said dispense location;

said wheel having an upward projection lying radially within said hole path, said projection forming a plurality of inclined guideways each positioned to guide an earplug into a corresponding one of said wheel holes

* * * * *